United States Patent
Chen et al.

(10) Patent No.: US 11,786,380 B2
(45) Date of Patent: Oct. 17, 2023

(54) BIONIC WRIST JOINT BASED ON ASYMMETRIC 3-RRR PARALLEL MECHANISM

(71) Applicant: HUAZHONG UNIVERSITY OF SCIENCE AND TECHNOLOGY, Hubei (CN)

(72) Inventors: Wen-Bin Chen, Hubei (CN); Hao Fu, Hubei (CN); Yu-Lin Zhang, Hubei (CN); Xiang Fan, Hubei (CN); Zhi-Jie Zhou, Hubei (CN); Cai-Hua Xiong, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 238 days.

(21) Appl. No.: 17/488,318

(22) Filed: Sep. 29, 2021

(65) Prior Publication Data

US 2022/0362039 A1  Nov. 17, 2022

(30) Foreign Application Priority Data

May 17, 2021  (CN) .......................... 202110538915.8

(51) Int. Cl.
  *A61F 2/58* (2006.01)
  *B25J 17/02* (2006.01)
  *A61F 2/68* (2006.01)
  *A61F 2/70* (2006.01)
  *A61F 2/50* (2006.01)

(52) U.S. Cl.
  CPC ................ *A61F 2/585* (2013.01); *A61F 2/68* (2013.01); *B25J 17/0283* (2013.01); *B25J 17/0291* (2013.01); *A61F 2002/5038* (2013.01); *A61F 2002/6836* (2013.01); *A61F 2002/701* (2013.01)

(58) Field of Classification Search
  CPC ........................................................ A61F 2/585
  See application file for complete search history.

(56) References Cited

FOREIGN PATENT DOCUMENTS

CN          108836582 A  *  11/2018  ............. A61F 2/585

* cited by examiner

*Primary Examiner* — David H Willse
(74) *Attorney, Agent, or Firm* — JCIPRNET

(57) ABSTRACT

The invention discloses a bionic wrist joint based on an asymmetric 3-RRR parallel mechanism, including: an asymmetric 3-RRR parallel mechanism and a drive unit. The asymmetric 3-RRR parallel mechanism includes: a moving platform, a first static platform, and three asymmetrically distributed parallel branch chains, wherein each branch chain includes a passive rod and an active rod. An end of the active rod is connected to the first static platform via the revolute pair, and another end thereof is connected to the passive rod via the revolute pair. The axes of the revolute pairs at two ends of the active rod form an axis included angle. Three axis included angles are different, the passive rod and the moving platform are connected by the revolute pair, and three axis included angles corresponding to the passive rods are different. The drive unit is configured to drive the asymmetric 3-RRR parallel mechanism to move.

18 Claims, 3 Drawing Sheets

BIONIC WRIST JOINT BASED ON ASYMMETRIC 3-RRR PARALLEL MECHANISM

CROSS-REFERENCE TO RELATED APPLICATION

This application claims the priority benefit of China application serial no. 202110538915.8, filed on May 17, 2021. The entirety of the above-mentioned patent application is hereby incorporated by reference herein and made a part of this specification.

BACKGROUND OF THE INVENTION

Field of the Invention

The invention belongs to the field of wrist joint simulation, and more specifically, to a bionic wrist joint based on an asymmetric 3-RRR parallel mechanism.

Description of Related Art

The human arm is a complex movement system composed of multiple bones and muscles. The coordinated control of these complex bones, muscles, and nerves produces the flexible and variable movement of the human arm, and thus a person's ability to manipulate objects and the convenience of life are significantly improved. Amputation caused by diseases and accidents seriously affects people's everyday life, destroys the mental health of patients, and disrupts normal social interaction. According to data from the Second China Disabled Population Sample Survey in 2006, the total number of people with disabilities in our country reached 83 million, accounting for 6.34% of the country's total population, in which there are 24 million people with physical disabilities, accounting for 29% of the disabled population, and in which 2.2 million of them have amputations. There are 4 million amputees worldwide. The population of amputees worldwide is increasing by 150,000 to 200,000 every year, and 30% of all amputees are upper-limb amputees. Patients with upper limb amputations face many difficulties in life, especially the lack of self-care ability. It is under this background that the demand for prosthetic research has gradually emerged.

At present, most prostheses just dwell on the concept of traditional prostheses. The appearance of traditional prostheses is human-like, the surface thereof has a certain degree of elasticity, but the traditional prostheses only have a decorative effect. Some prostheses provide a small amount of passive degrees of freedom, and the joints thereof need to be adjusted to the required posture with the healthy side during use. This kind of prostheses has preliminary use functions, but are not convenient for people with disabilities to operate during use, have limited functions, and do not meet the requirements of multi-degree freedom and dexterity.

At present, research initiated by the Defense Advanced Research Projects Agency (DARPA) of the United States has developed a representative modular prosthetic arm—the revolutionary prosthesis. The wrist joint thereof may complete the two-degree-of-freedom motion of flexion, extension, ulnar deviation and radial deviation just like a human wrist joint. Although it may move as flexibly as a human wrist, the configuration of the prosthesis determines that the forearm prosthesis has a longer body. The higher requirements for the length of the severed forearm of the disabled may not meet the needs of most patients with a severed forearm, and therefore the scope of application for the disabled with different levels of severance is limited. Domestic prosthetic wrist joints include cable-controlled passive prostheses, while power prostheses adopt differential mechanisms, gears, etc.

It may be seen that the prior art has the technical issues of longer body and poor bionic effect.

SUMMARY OF THE INVENTION

In view of the above defects or improvement requirements of the prior art, the invention provides a bionic wrist joint based on an asymmetric 3-RRR parallel mechanism, thereby solving the technical issues of longer body and poor bionic effect in the prior art.

To achieve the above object, the invention provides a bionic wrist joint based on an asymmetric 3-RRR parallel mechanism including: an asymmetric 3-RRR parallel mechanism and a drive unit,
  wherein the asymmetric 3-RRR parallel mechanism includes: a moving platform, a first static platform, and three asymmetrically distributed parallel branch chains, each of the branch chains includes a passive rod and an active rod;
  an end of the active rod is connected to the first static platform via the revolute pair, and another end thereof is connected to the passive rod via the revolute pair, the axes of the revolute pairs at two ends of the active rod form an axis included angle, the three active rods form three different axis included angles, the passive rod and the moving platform are connected by the revolute pair, and the three axis included angles corresponding to the three passive rods are also different;
  the drive unit is configured to drive the asymmetric 3-RRR parallel mechanism to move.

Further, the three revolute pairs connected to the three active rods on the three branch chains and the first static platform are distributed on a same circle, every two revolute pairs are connected to a center of the circle to form an included angle, the three revolute pairs are combined in pairs to form three included angles, and the three included angles are different from one another.

Further, the three revolute pairs connected to the three passive rods on the three branch chains and the moving platform are distributed on a same circle, and an included angle formed between pairs of revolute pairs of the passive rods connected to the moving platform and a center of the circle is the same as a corresponding included angle of the active rod on the same branch chain.

Further, a range of the axis included angle of the active rod is 75° to 95°, and a range of the axis included angle of the passive rod is 70° to 100°.

Further, a range of the included angle formed by the connection of the two revolute pairs to the center of the circle is 115° to 125°, and a sum of the three included angles is 360°.

Further, the active rods and the passive rods are all spherical joint linkages.

Further, the distribution of the three branch chains is:
  taking a center of the asymmetric 3-RRR parallel mechanism as a center of a sphere, dividing a space into a plurality of continuous spherical surfaces with radii having equal difference at equal intervals, wherein adjacent spherical surfaces form one hollow sphere space, wherein in the three branch chains, all of the passive rods are distributed in one hollow sphere space, and all of the active rods are distributed in a plurality of adjacent hollow sphere spaces.

Further, the distribution of the three branch chains is: taking a center of the asymmetric 3-RRR parallel mechanism as a center of a sphere, dividing a space into a plurality of continuous spherical surfaces with radii having equal difference at equal intervals, wherein adjacent spherical surfaces form one hollow sphere space, wherein in the three branch chains, all of the passive rods are distributed in a plurality of adjacent hollow sphere spaces, and all of the active rods are distributed in a plurality of adjacent hollow sphere spaces.

Further, the hollow sphere spaces in which the active rods are distributed and the hollow sphere spaces in which the passive rods are distributed are not overlapped.

Further, the drive unit includes three motors and three reducers arranged in parallel. Each of the active rods is connected to one motor and one reducer, the motor is configured to drive the active rod to move, and the reducer is configured to increase an output torque of the motor.

Further, the drive unit further includes: a pair of bevel gears, wherein the pair of bevel gears are respectively connected to a rotating shaft of the active rod and a flange shaft via a key connection.

Further, the asymmetric 3-RRR parallel mechanism further includes: a second static platform, wherein the second static platform is fixedly connected to the first static platform and configured to form a revolute pair of the pair of bevel gears.

Further, a rotation of the active rods drives the passive rods and the moving platform connected to the passive rods to move, thereby implementing flexion, extension, ulnar deviation and radial deviation of the bionic wrist joint, as well as pronation and supination of forearm.

Generally speaking, compared with the prior art, the above technical solutions conceived by the invention may achieve the following beneficial effects:

(1) By introducing the 3-RRR parallel mechanism, the wrist joint designed in the invention may significantly reduce the overall size of the simulated wrist joint while holding a certain load capacity. The mechanism thereof has high motion accuracy, light total mechanism weight, and high load. In addition, the 3-RRR parallel mechanism in the invention is asymmetrically distributed, so that the three degrees of freedom of the parallel mechanism have different ranges of motion, so as to be more compatible with the range of motion of the human wrist.

(2) The invention takes into account the different ranges of motion of flexion, extension, ulnar deviation and radial deviation of wrist joint, as well as supination and pronation of forearm of normal human, and optimizes the distribution of the three revolute pairs connected to the active rods and the first static platform, and optimizes the axis included angles corresponding to the active and passive rods, so that the three revolute ranges of the moving platform are different in each direction, and are more compatible with the range of motion of a normal human wrist joint.

(3) In the invention, the active rods and the passive rods are arranged in different hollow sphere spaces so that the interference of the linkages of the mechanism of the invention may be alleviated to achieve a wider range of motion than the traditional symmetric 3-RRR parallel mechanism.

(4) The 3-RRR parallel mechanism designed in the invention may reduce the power requirement of a single motor. Coupled with the parallel arrangement of the motors and reducers, the length of the entire apparatus is significantly reduced. Compared with the current mainstream power prostheses in the world, there is the advantage of better adapting to the disabled with longer residual limb length.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

In all the figures, the same reference numerals are used to denote the same elements or structures, wherein.

1: moving platform, 2: passive rod, 3: active rod, 4: pair of bevel gears, 5: first static platform, 6: second static platform, 7: first transition member, 8: flange shaft, 9: second transition member, 10: reducer, 11: first fixing plate, 12: connecting pillar, 13: motor, and 14: second fixing plate.

DESCRIPTION OF THE EMBODIMENTS

In order to make the objectives, technical solutions, and advantages of the invention clearer, the invention is further described in detail below in conjunction with the accompanying figures and embodiments. It should be understood that the specific embodiments described herein are only used to explain the invention, and are not intended to limit the invention. In addition, the technical features involved in the various embodiments of the invention described below may be combined with each other as long as there is no conflict with each other.

Figure 1:
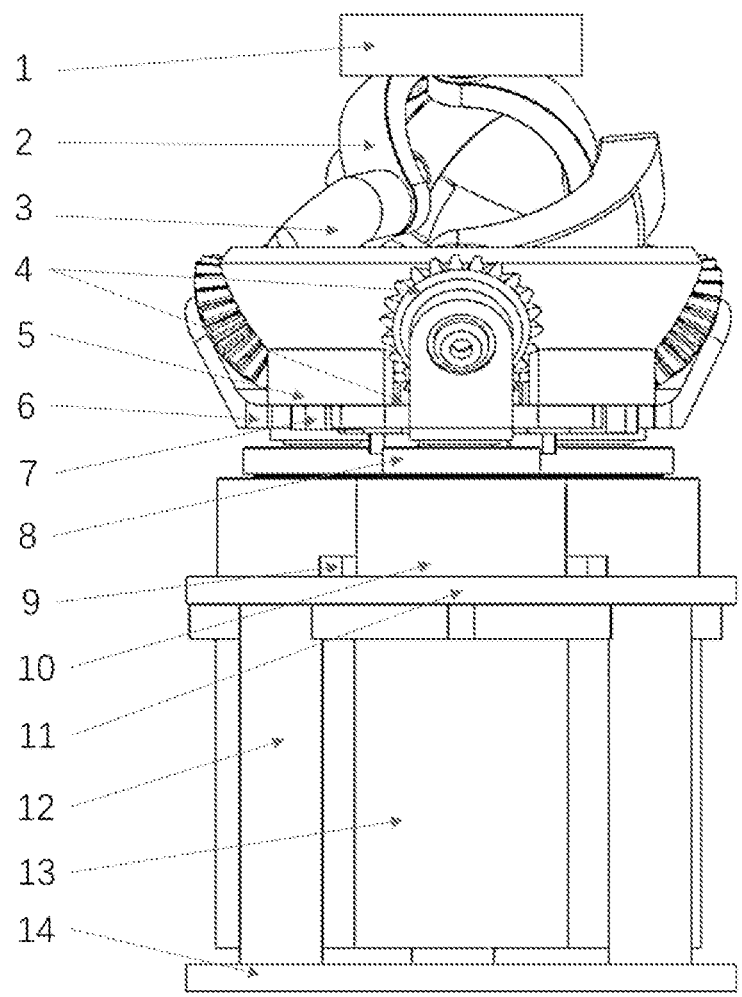
FIG. 1 is a front view of a bionic wrist joint based on an asymmetric 3-RRR parallel mechanism provided by an embodiment of the invention.
Figure 2:
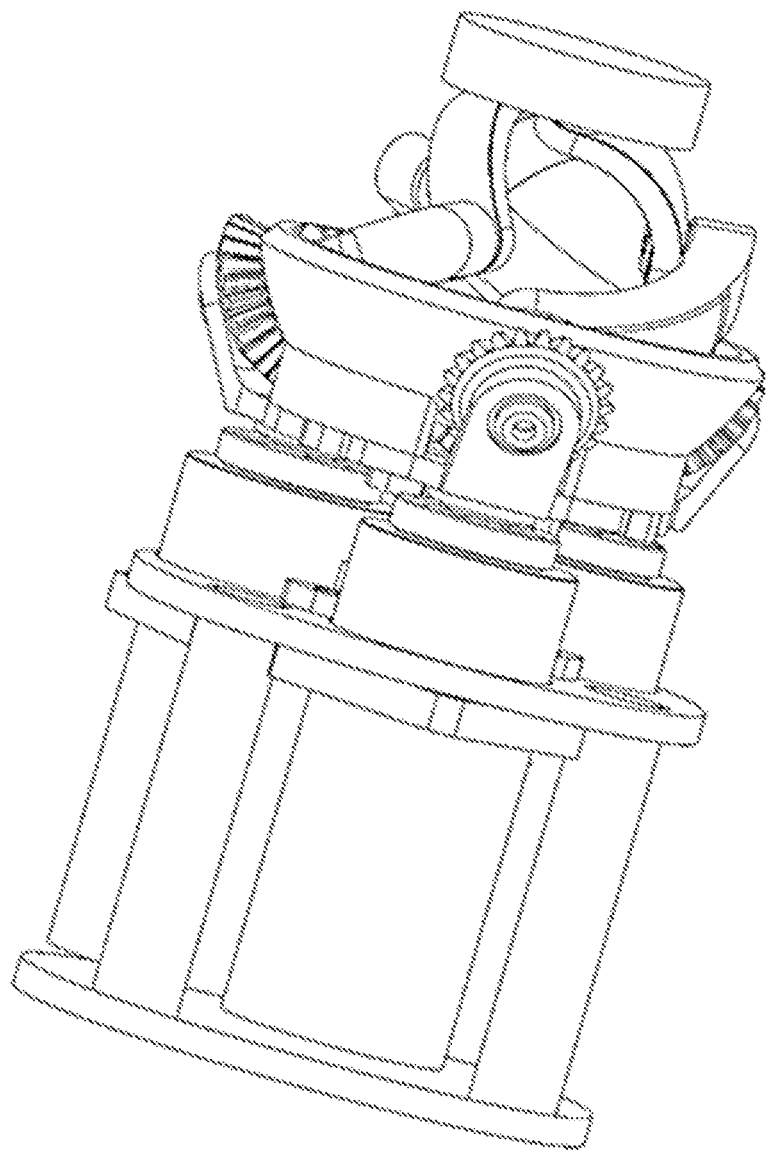
FIG. 2 is a perspective view of a bionic wrist joint based on an asymmetric 3-RRR parallel mechanism provided by an embodiment of the invention.

As shown in FIGS. 1 and 2, a bionic wrist joint based on an asymmetric 3-RRR parallel mechanism includes: an asymmetric 3-RRR parallel mechanism and a drive unit, wherein the asymmetric 3-RRR parallel mechanism includes: passive rods 2, active rods 3, and the number of the passive rods is 3 and the number of the active rods is 3. The active and passive rods are connected by the revolute pairs, the active rods are connected to the first static platform 5 via the revolute pairs, and the passive rods are connected to the moving platform 1 via the revolute pairs. The second static platform 6 and the first static platform 5 are fixedly connected by screw fastening for the constraint of the revolute pair of a pair of bevel gears 4. The pair of bevel gears 4 are respectively connected to the rotating shaft of the active rod and a flange shaft 8 via a key connection. The bevel gears are configured to connect the parallel drive shafts to the rotating shafts of the active rods which are intersected at one point, and the shaft angle of the bevel gears is determined by the included angle between the axis of rotation of the active rods and the static platform. The flange shaft is connected to the reducer 10 by screw fastening. The first static platform and the second static platform are configured to constrain the active rods, and the moving platform is configured to constrain the passive rods. The active rods are active spherical joint linkage. The three active spherical joint linkages are non-uniformly distributed on the same ring, and the passive rods are configured to link the active rods and the moving platform.

The revolute pairs connected to the three active rods and the first static platform are distributed on the same circle. The range of the included angle formed by the connection of the two revolute pairs and the center of the circle is 120°±5°, the specific values of the three included angles are different, and the sum of the three included angles is 360°. For the revolute pair connected to the active rod and the first static platform and the revolute pair connected to the passive rod, the ranges of axis included angles of the two revolute pair are (75°, 95°), and the axis included angles of the three revolute pairs corresponding to the three active rods are different. The revolute pairs connected to the three passive rods and the moving platform are distributed on the same circle. The range of the included angle formed by the connection of the two revolute pairs and the center of the circle is 120°±5°, the specific values of the three included angles are different, and the sum of the three included angles is 360°. At the same time, the included angle between the revolute pairs connected to the passive rods and the moving platform is the same as the included angle of the active rod connected thereto on the first static platform.

Taking the center of the parallel mechanism as the center of the sphere, the space is divided into a plurality of continuous spherical surfaces with radii having equal difference at equal intervals, and adjacent spherical surfaces form one hollow sphere space. The axes of the revolute pairs of the three active rods and the three passive rods are intersected at the center of the sphere. In the three branch chains, all of the passive rods are distributed in one hollow sphere space or a plurality of hollow sphere spaces, and all of the active rods are distributed in a plurality of adjacent hollow sphere spaces. All of the active rods are distributed in a plurality of adjacent hollow sphere spaces, namely each of the active rods continuously occupies a plurality of continuous hollow sphere spaces.

Each of the active rods is equipped with one motor and one reducer, and three groups of motors and reducers are arranged in parallel.

The drive unit includes: a frame, motors 13, and reducers 10. A first fixing plate 11, a second fixing plate 14, and connecting pillars 12 are fixedly connected by screw fastening to form the frame. The motor is fixedly connected to the reducer, the reducer is fixedly connected to the frame by screw fastening, and the output surface of the reducer is fixed with the flange shaft by screw fastening. The frame is fixed with a first transition member 7, a second transition member 9, and a second static platform by screw fastening.

The range of motion of the wrist joint is shown in Table 1. The asymmetrical design of the linkages of the 3-RRR parallel mechanism in the invention makes the range of motion of the three degrees of freedom of the parallel mechanism different. By optimizing the parameters, the range of motion of the mechanism is compatible with the range of motion of flexion, extension, ulnar deviation and radial deviation of a normal human wrist joint, as well as supination and pronation of forearm. At the same time, the arrangement of different hollow sphere spaces of the rods may relieve the interference of the linkages of the mechanism of the invention to achieve a wider range of motion than the traditional symmetric 3-RRR parallel mechanism.

TABLE 1

| Form of motion | Human wrist joint function range | Range of motion of dexterous wrist |
|---|---|---|
| Pronation and supination | (−50°, 50°) | (−75°, 80°) |
| Flexion and extension | (−60°, 60°) | (−66°, 24°) |
| Radial and ulnar deviation | (−20°, 40°) | (−30°, 50°) |

Figure 3:
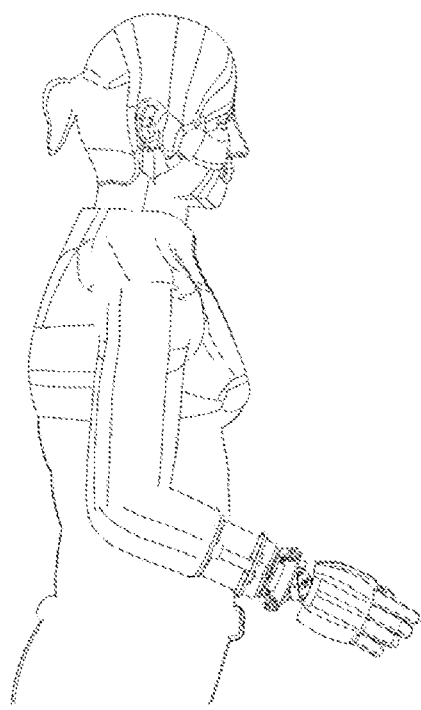
FIG. 3 is a schematic diagram of the wear relationship between a bionic wrist joint and a patient with a severed forearm provided by an embodiment of the invention.
Figure 4:
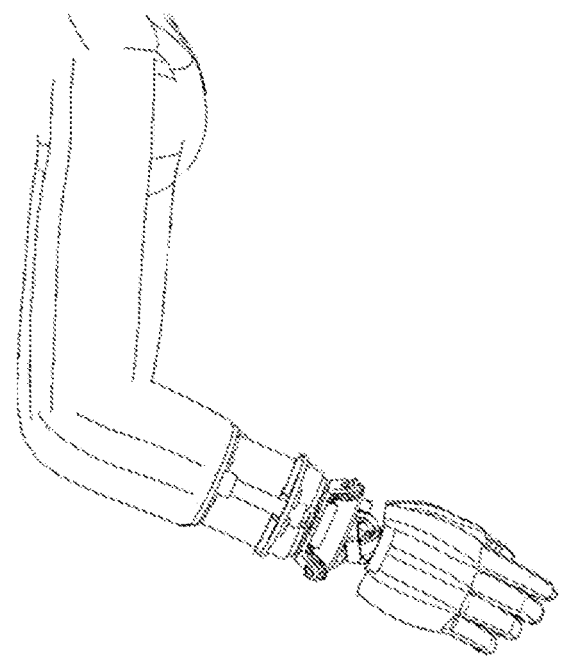
FIG. 4 is a detailed diagram of the wear relationship between a bionic wrist joint and a patient with a severed forearm provided by an embodiment of the invention.

The outer diameter of the apparatus provided by the invention is about 80 mm, and the overall length thereof is about 142 mm. Taking the center of the parallel mechanism as the starting point of the moment arm, the wrist joint load is about 2 N·m. For forearm amputees, as shown in FIGS. 3 and 4, the apparatus provided by the invention may be worn on the end of the patient's amputation after being fixed with a receiving cavity (the receiving cavity is not included in the figures), and the moving platform of the apparatus may be connected to the prosthetic hand. The bionic wrist joint apparatus provided by the invention has a compact structure, an overall size and an outer diameter close to that of a human arm, and may achieve better appearance effects. The range of motion of the apparatus is compatible with a normal wrist joint, and has a certain load capacity to better reproduce the function of the human wrist joint.

It is easy for those skilled in the art to understand that the above are only preferred embodiments of the invention and are not intended to limit the invention. Any modification, equivalent replacement, and improvement made within the spirit and principles of the invention should be included in the protection scope of the invention.

What is claimed is:

1. A bionic wrist joint based on an asymmetric 3-RRR parallel mechanism, comprising: an asymmetric 3-RRR parallel mechanism and a drive unit,
    wherein the asymmetric 3-RRR parallel mechanism comprises: a moving platform, a first static platform, and three asymmetrically distributed parallel branch chains, wherein each of the branch chains comprises a passive rod and an active rod;
    an end of the active rod is connected to the first static platform via a revolute pair, and another end thereof is connected to the passive rod via the revolute pair, the axes of the revolute pairs at two ends of the active rod form an axis included angle, three active rods form three different axis included angles, the passive rod and the moving platform are connected by the revolute pair, and three axis included angles corresponding to three passive rods are also different;
    the drive unit is configured to drive the asymmetric 3-RRR parallel mechanism to move.

2. The bionic wrist joint based on the asymmetric 3-RRR parallel mechanism of claim 1, wherein the three revolute pairs connected to the three active rods on the three branch chains and the first static platform are distributed on a same circle, every two revolute pairs are connected to a center of the circle to form an included angle, the three revolute pairs are combined in pairs to form three included angles, and the three included angles are different from one another.

3. The bionic wrist joint based on the asymmetric 3-RRR parallel mechanism of claim 2, wherein the three revolute pairs connected to the three passive rods on the three branch chains and the moving platform are distributed on a same circle, and an included angle formed between pairs of revolute pairs of the passive rods connected to the moving platform and a center of the circle is the same as a corresponding included angle of the active rod on the same branch chain.

4. The bionic wrist joint based on the asymmetric 3-RRR parallel mechanism of claim 1, wherein a range of the axis included angle of the active rod is 75° to 95°.

5. The bionic wrist joint based on the asymmetric 3-RRR parallel mechanism of claim 1, wherein a range of the axis included angle of the passive rod is 70° to 100°.

6. The bionic wrist joint based on the asymmetric 3-RRR parallel mechanism of claim 2, wherein a range of the included angle formed by the connection of the two revolute pairs and the center of the circle is 115° to 125°, and a sum of the three included angles is 360°.

7. The bionic wrist joint based on the asymmetric 3-RRR parallel mechanism of claim 1, wherein a distribution of the three branch chains is:
    taking a center of the asymmetric 3-RRR parallel mechanism as a center of a sphere, dividing a space into a plurality of continuous spherical surfaces with radii having equal difference at equal intervals, wherein adjacent spherical surfaces form one hollow sphere space, wherein in the three branch chains, all of the passive rods are distributed in one hollow sphere space, and all of the active rods are distributed in a plurality of adjacent hollow sphere spaces.

8. The bionic wrist joint based on the asymmetric 3-RRR parallel mechanism of claim 1, wherein a distribution of the three branch chains is:
    taking a center of the asymmetric 3-RRR parallel mechanism as a center of a sphere, dividing a space into a plurality of continuous spherical surfaces with radii having equal difference at equal intervals, wherein adjacent spherical surfaces form one hollow sphere space, wherein in the three branch chains, all of the passive rods are distributed in a plurality of adjacent hollow sphere spaces, and all of the active rods are distributed in a plurality of adjacent hollow sphere spaces.

9. The bionic wrist joint based on the asymmetric 3-RRR parallel mechanism of claim 7, wherein the hollow sphere spaces in which the active rods are distributed and the hollow sphere spaces in which the passive rods are distributed are not overlapped.

10. The bionic wrist joint based on the asymmetric 3-RRR parallel mechanism of claim 1, wherein the drive unit comprises three motors and three reducers arranged in parallel, each of the active rods is connected to one motor and one reducer, the motor is configured to drive the active rod to move, and the reducer is configured to increase an output torque of the motor.

11. The bionic wrist joint based on the asymmetric 3-RRR parallel mechanism of claim 2, wherein a range of the axis included angle of the active rod is 75° to 95°.

12. The bionic wrist joint based on the asymmetric 3-RRR parallel mechanism of claim 3, wherein a range of the axis included angle of the active rod is 75° to 95°.

13. The bionic wrist joint based on the asymmetric 3-RRR parallel mechanism of claim 2, wherein a range of the axis included angle of the passive rod is 70° to 100°.

14. The bionic wrist joint based on the asymmetric 3-RRR parallel mechanism of claim 3, wherein a range of the axis included angle of the passive rod is 70° to 100°.

15. The bionic wrist joint based on the asymmetric 3-RRR parallel mechanism of claim 3, wherein a range of the included angle formed by the connection of the two revolute pairs and the center of the circle is 115° to 125°, and a sum of the three included angles is 360°.

16. The bionic wrist joint based on the asymmetric 3-RRR parallel mechanism of claim 8, wherein the hollow sphere spaces in which the active rods are distributed and the hollow sphere spaces in which the passive rods are distributed are not overlapped.

17. The bionic wrist joint based on the asymmetric 3-RRR parallel mechanism of claim 2, wherein the drive unit comprises three motors and three reducers arranged in parallel, each of the active rods is connected to one motor and one reducer, the motor is configured to drive the active rod to move, and the reducer is configured to increase an output torque of the motor.

18. The bionic wrist joint based on the asymmetric 3-RRR parallel mechanism of claim 3, wherein the drive unit comprises three motors and three reducers arranged in parallel, each of the active rods is connected to one motor and one reducer, the motor is configured to drive the active rod to move, and the reducer is configured to increase an output torque of the motor.

* * * * *